United States Patent [19]

Vogt et al.

[11] Patent Number: 4,471,148
[45] Date of Patent: Sep. 11, 1984

[54] PROCESS FOR MAKING CATALYTICALLY ACTIVE ALUMINOSILICATES AND THEIR USES

[75] Inventors: Wilhelm Vogt, Hürth; Hermann Glaser, Erfstadt; Jürgen Koch, Brühl; Günter Lenz, Frechen, all of Fed. Rep. of Germany

[73] Assignee: Hoechst Aktiengesellschaft, Fed. Rep. of Germany

[21] Appl. No.: 455,279

[22] Filed: Jan. 3, 1983

[30] Foreign Application Priority Data

Jan. 28, 1982 [DE] Fed. Rep. of Germany ....... 3202657

[51] Int. Cl.$^3$ .............................................. C07C 1/20
[52] U.S. Cl. .................................... 585/640; 585/408; 585/469; 585/733; 502/64; 502/71; 423/334
[58] Field of Search ................ 585/408, 469, 640, 639; 252/449, 455 Z; 423/334; 502/235, 73, 202, 263, 332

[56] References Cited

U.S. PATENT DOCUMENTS

| 3,252,757 | 5/1966 | Granquist | 502/80 |
| 3,359,068 | 12/1967 | Michalko | 502/60 |
| 4,333,859 | 6/1982 | Vaughan et al. | 502/68 |

FOREIGN PATENT DOCUMENTS

| 483842 | 8/1975 | Australia | 502/79 |
| 1142905 | 10/1980 | Canada | 502/79 |
| 0017027 | 10/1980 | European Pat. Off. | |
| 0040104 | 11/1981 | European Pat. Off. | 502/79 |
| 248635 | 2/1968 | U.S.S.R. | 502/79 |

OTHER PUBLICATIONS

Römpps–Chemie–Lexicon, 8th Edition, ed. by Otto-Albrecht Neumüller, Frankh'sche Verlagshandlung, W. Keller & Co., Stuttgart, 1979, p. 498.
Howley, "Condensed Chemical Dictionary", (Van Nostrand, 1977), pp. 122 and 413.

Primary Examiner—Delbert E. Gantz
Assistant Examiner—A. Pal
Attorney, Agent, or Firm—Connolly and Hutz

[57] ABSTRACT

The disclosure relates to a process for making catalytically active aluminosilicates from glasses by hydrothermal cristallization. The hydrothermal cristallization is more particularly effected in the presence of an aqueous solution of an inorganic alkali metal compound producing an alkaline reaction but in the absence of an amine. Useful alkali metal compounds comprise alkali metal carbonate, water glass, alkali metal hydroxide or alkali metal phosphate.

The catalytically active aluminosilicates can be used for dehydrating alcohols, ethers and other oxygen-containing organic compounds with formation of hydrocarbons, or for isomerizing or alkylating hydrocarbons.

12 Claims, 1 Drawing Figure

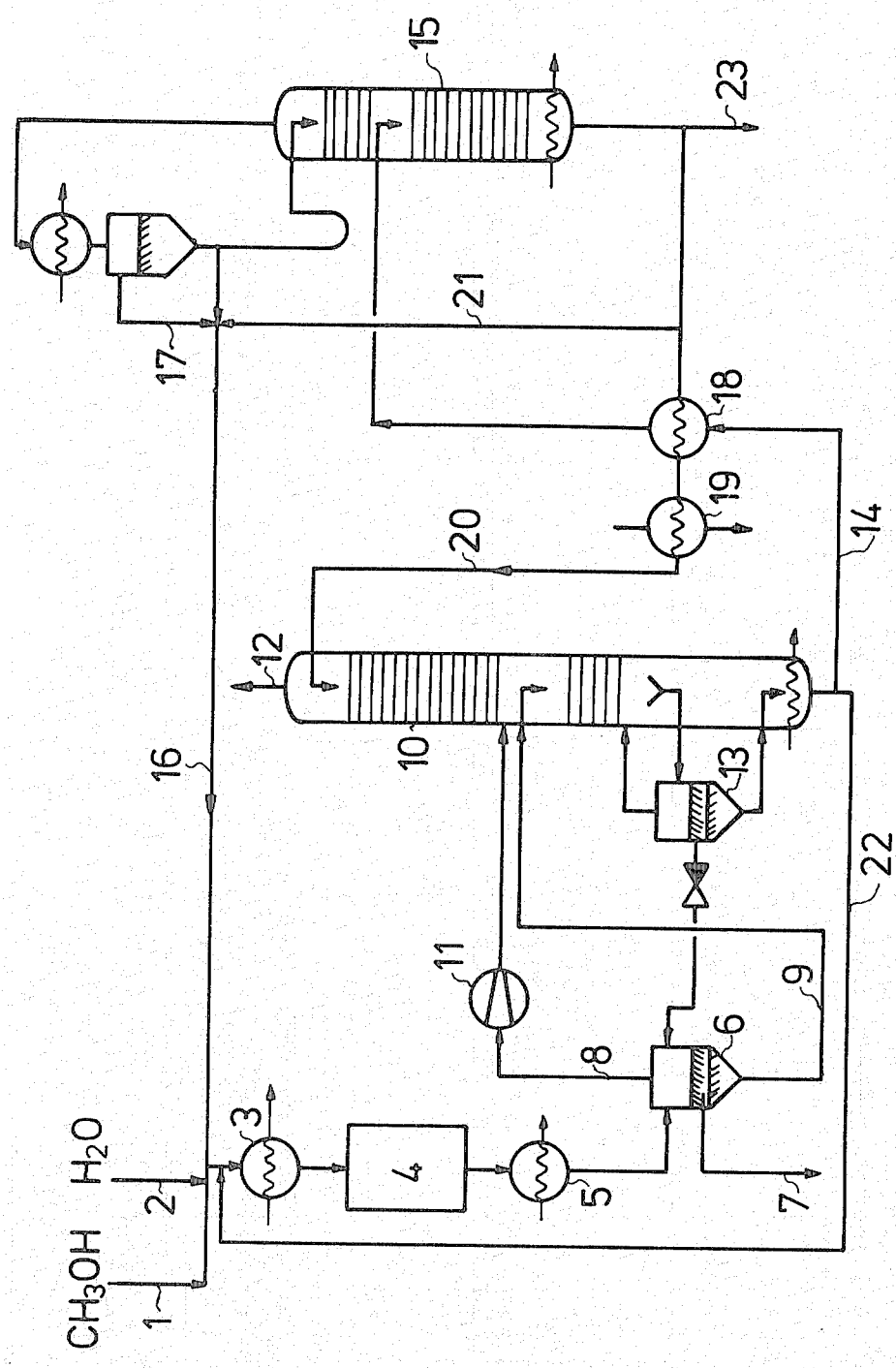

PROCESS FOR MAKING CATALYTICALLY ACTIVE ALUMINOSILICATES AND THEIR USES

The present invention relates to a process for making catalytically active aluminosilicates from glasses by hydrothermal cristallization, and to their uses for dehydrating oxygen-containing organic compounds, and isomerizing or alkylating hydrocarbons.

A process for making a catalytically active zeolite by subjecting glass to hydrothermal cristallization in the presence of an amine such as hexamethylene diamine, the reaction mixture containing more than 25 weight % solid matter, has already been described (cf. European Patent Application No. EP-A1-0 017 027).

The zeolites so made can be used as catalysts for reacting lower alcohols or dialkylethers to aromatic hydrocarbons or olefins.

A further process for making aluminosilicates which are useful as catalysts or carriers has been described (cf. European Patent Application EP-A1-0 002 900) wherein a mixture of silicates, aluminum oxide, an alkali metal compound and water is reacted at temperatures of 80° to 210° C., under pressures of about 5 to 28 bars, over a period of less than 4 hours and in the presence of one or more substituted secondary or tertiary amines or unsubstituted tertiary amines.

In these known processes, it is necessary to have considerable quantities of amines act upon the glass or mixture consisting of silicates, aluminum oxide and an alkali metal compound so as to effect formation of aluminosilicates. As a result, their production is rendered expensive and the removal of waste material is rendered problematic.

We have now unexpectedly found that catalytically active aluminosilicates are even formed in the absence of amines by subjecting glass, especially of the borosilicate type, to hydrothermal treatment. To this end, the invention provides for the hydrothermal crystallization to be effected in the presence of an aqueous solution of an inorganic alkali metal compound producing an alkaline reaction.

Preferred and optional features of the present invention provide:

(a) for the inorganic alkali metal compound to be an alkali metal carbonate;
(b) for the inorganic alkali metal compound to be water glass;
(c) for the inorganic alkali metal compound to be an alkali metal hydroxide;
(d) for the inorganic alkali metal compound to be an alkali metal phosphate;
(e) for glass powder consisting of particles with a size smaller than 1 mm to be treated with an aqueous solution containing 1 to 40 weight % of inorganic alkali metal compound, the treatment being effected over a period of 10 to 500 hours, preferably 50 to 200 hours, at temperatures of 120° to 200° C., inside an autoclave.

The aluminosilicates made by the process of this invention are present in Na-form. If it is desirable for them to be present in H-form for catalytic use, it is possible for the aluminosilicates in Na-form to be washed with the ammonium salt of a mineral acid and in this way to be converted to $NH_4$-form which can successively by converted to H-form by annealing treatment at 300° to 600° C. Aluminosilicate in H-form can also be obtained in customary manner by treating Na-form with a mineral acid.

Microscopic investigation of the aluminosilicates of this invention has shown the bulk proportion to consist of particles with a size approximately the same as that of the glass powder, and a minor proportion to consist of particles with a size of several $\mu$, which was initially not present. After conversion to H-form, for example, the two proportions are catalytically active; in other words, catalytic activity originates at least partially from the surface of those particles which were glass particles prior to hydrothermal treatment. By using appropriately shaped feed material, it is possible directly to use the aluminosilicates of this invention as fixed bed or fluidized bed catalysts.

Fixed bed and fluidized bed catalysts can also be obtained by blending the aluminosilicates of this invention with strengthening materials, e.g. TONSIL (this is a registered Trade Mark) and making them into moulded articles.

In clear contrast with prior synthetic aluminosilicates, those of this invention present a strikingly broad band of strong intensity within the region of 12.5 to $13.5 \cdot 10^{-10}$ m, in their X-ray diagram.

The catalysts made in the following Examples 1 to 4 from aluminosilicates of this invention were used in an apparatus, such as that illustrated diagrammatically in the accompanying drawing, for making hydrocarbons by splitting methanol in the presence of water.

With reference to the drawing:

Methanol and water in a ratio by volume of 1:1 are pumped through feed lines (1, 2) into evaporator 3. The evaporated methanol/water-mixture is introduced at a temperature of 320° C. and under a pressure of 1.2 bar into fixed bed reactor 4 having a catalyst of extruded material placed therein. Gas mixture coming from solid bed reactor 4 is cooled to about 25° C. in condenser 5 and separated in separator 6 into an oil phase, water phase and gas phase, respectively. The oil phase consisting of higher aliphates and aromates is removed through line 7. The aqueous phase is pumped through line 9 to the expelling portion of scrubbng column 10, whilst the gas phase is introduced through line 8 and compressor 11 into scrubbing column 10 at a level lower than the absorption portion, under a pressure of 20 bars. Water at 25° C. is used for separating methanol which remained unreacted in fixed bed reactor 4 and dimethylether which is formed as an intermediary product, from the gas mixture is introduced through line 20 into the head portion of scrubbing column 10. A gas mixture consisting essentially of hydrocarbons is taken from the scrubbing column through line 12.

Methanol which remains unreacted on being passed through fixed bed reactor 4 and formed dimethylether together with scrubbing water are taken from the bottom portion of scrubbing column 10 and introduced into stripping column 15 through line 14. Methanol (through line 16) and gaseous dimethylether (through line 17) are recycled from the head portion of stripping column 15 through evaporator 3 into fixed bed reactor 4.

EXAMPLE 1

500 g DURAN glass powder (DURAN is a registered Trade Mark) consisting of particles with a size of less than 200$\mu$ and 2 liters of a 3% sodium carbonate solution were introduced into a 5 liter stainless steel autoclave, which was maintained over a period of 5 days at 175° C. with continuous agitation. After cooling, fine-particulate product was taken from the autoclave, washed with water and boiled three times with a 10% ammonium nitrate solution so as to be freed from alkali. The residue filtered off was dried at 60° to 110° C. and annealed for 2 hours at 500° C.

The aluminosilicate which now was in H-form was mixed with TONSIL (this is a registered Trade Mark) as a binder in a ratio by weight of 4:1 and admitted to a roll extruder, and made into extruded material 3 mm in diameter.

The extruded material was used in fixed bed reactor 4 of the apparatus described hereinabove; the catalyst efficiency was 92 g ethylene, 118 g propylene and 31 g butylene per liter catalyst per hour.

EXAMPLE 2

Example 1 was repeated but a 7.3% water glass solution of the formula $Na_2(SiO_3)_{2.8}$ was substituted for the 3% sodium carbonate solution.

The extruded material used in fixed bed reactor 4 of the apparatus described hereinabove had a catalytic efficiency of 65 g ethylene, 84 g propylene and 22 g butylene per liter catalyst per hour.

EXAMPLE 3

Example 1 was repeated but a 2.3% sodium hydroxide solution was substituted for the 3% sodium carbonate solution.

The extruded material placed in fixed bed reactor 4 of the apparatus described hereinabove had a catalytic efficiency of 36 g ethylene, 68 g propylene and 17 g butylene per liter catalyst per hour.

EXAMPLE 4

500 g DURAN glass powder (DURAN is a registered Trade Mark) consisting of particles with a size of less than 300μ and 2 liters of a 38% solution of trisodium phosphate dodecahydrate ($Na_3PO_4.12H_2O$) were placed in a 5 liter stainless steel autoclave, which was maintained over a period of 6 days at 175° C. with continuous agitation. After cooling, fine-particulate material was taken from the autoclave, washed with water and boiled three times with 10% ammonium nitrate solution so as to be freed from alkali. The residue filtered off was dried at 60° to 110° C. and annealed for 2 hours at 500° C. The aluminosilicate which now was in H-form was mixed with TONSIL (this is a registered Trade Mark) as a binder in the ratio by weight of 4:1 and admitted to a roll extruder and extruded to material 3 mm in diameter.

The extruded material was used in fixed bed reactor 4 of the apparatus described hereinabove. It had a catalytic efficiency of 60 g ethylene, 100 g propylene and 26 g butylene per liter catalyst per hour.

EXAMPLE 5

50 milliliter alumino-silicate in H-form, prepared in the manner described in Example 1, was placed in a quartz reactor. The aluminosilicate was heated to 330° C. and a vaporous mixture of benzene and methanol in a molar ratio of 2:1 was passed over it at a weight hourly space velocity of 1. As a result, the temperature increased to 365° C. Resulting condensate was collected over a period of 40 minutes, separated into an organic phase and aqueous phase, and analyzed. More than 95% of the methanol and about 25% of the benzene were found to have underwent conversion. 15% of the benzene used was converted to toluene and the balance to higher alkylated aromates.

EXAMPLE 6

50 milliliter aluminosilicate in H-form, made as described in Example 1, was placed in a quartz reactor. The aluminosilicate was heated to 340° C., 360° C. and 380° C., respectively, and vaporous o-xylene was passed over it at a weight hourly space velocity of 1. Resulting condensate was collected each time over a period of 40 minutes, and analyzed.

The degree of isomerization is indicated in the following Table:

| Reaction temperature °C. | o-xylene % | m-xylene + p-xylene % |
|---|---|---|
| 340 | 41 | 58 |
| 360 | 30 | 67 |
| 380 | 28 | 68 |

We claim:

1. A process for making active aluminosilicates from glasses by hydrothermal crystallization, which comprises introducing an essentially amine-free mixture comprising (1) a borosilicate glass powder consisting essentially of particles with a size smaller than 1000 μm and (2) an aqueous solution containing 1 to 40 weight % of an alkali metal phosphate into an autoclave; maintaining said mixture over a period of 10 to 500 hours at a temperature of 120° and 200° C., in the absence of an amine, with continuous agitation; cooling the resulting fine particulate product and taking it from the autoclave; and washing the product with water.

2. The process as claimed in claim 1, wherein the product washed with water is boiled with an ammonium nitrate solution so as to be freed from alkali and wherein the residue filtered off is dried at 60° to 110° C. and calcined.

3. The process as claimed in claim 1, wherein said mixture is maintained over a period of 50 to 200 hours at temperatures of 120° to 200° C. with continuous agitation.

4. A process for making active aluminosilicates from glasses by hydrothermal crystallization, which comprises introducing an essentially amine-free mixture comprising (1) a borosilicate glass powder consisting essentially of particles with a size smaller than 1000 μm and (2) an aqueous solution containing 1 to 40 weight % of an alkali metal carbonate into an autoclave; maintaining said mixture over a period of 10 to 500 hours at a temperature of 120° to 200° C., in the absence of an amine, with continuous agitation; cooling the resulting fine-particulate product and taking it from the autoclave; and washing the product with water.

5. The process as claimed in claim 4, wherein the product washed with water is boiled with an ammonium nitrate solution so as to be freed from alkali and wherein the residue filtered off is dried at 60° to 110° C. and calcined.

6. The process as claimed in claim 4, wherein said mixture is maintained over a period of 50 to 200 hours at temperatures of 120° to 200° C. with continuous agitation.

7. A process for making active aluminosilicate from glasses by hydrothermal crystallization, which comprises introducing an essentially amine-free mixture comprising (1) a borosilicate glass powder consisting essentially of particles with a size smaller than 1000 μm and (2) an aqueous solution containing 1 to 40 weight % of an alkali metal hydroxide into an autoclave; maintaining said mixture over a period of 10 to 400 hours at a temperature of 120° to 200° C., in the absence of an amine, with continuous agitation; cooling the resulting fine-particulate product and taking it from the autoclave; and washing the product with water.

8. The process as claimed in claim 7, wherein the product washed with water is boiled with an ammonium nitrate solution so as to be freed from alkali and wherein the residue filtered off is dried at 60° to 110° C. and calcined.

9. The process as claimed in claim 7, wherein said mixture is maintained over a period of 50 to 200 hours at temperatures of 120° to 200° C. with continuous agitation.

10. A process for dehydrating an oxygen-containing organic compound so as to effect the formation of hydrocarbons, which comprises effecting the dehydration with the use of an aluminosilicate made by the process as claimed in claim 1.

11. A process for dehydrating an oxygen-containing organic compound so as to effect the formation of hydrocarbons, which comprises effecting the dehydration with the use of an aluminosilicate made by the process as claimed in claim 4.

12. A process for dehydrating an oxygen-containing organic compound so as to effect the formation of hydrocarbons, which comprises effecting the dehydration with the use of an aluminosilicate made by the process as claimed in claim 7.

* * * * *